US00PP17110P3

(12) United States Plant Patent
Krsnak

(10) Patent No.: US PP17,110 P3
(45) Date of Patent: Sep. 19, 2006

(54) LILAC PLANT NAMED 'NEW PATRIOT VARIEGATED-LILAC'

(50) Latin Name: ***Syringa* sp.**
Varietal Denomination: New Patriot Variegated-Lilac

(76) Inventor: Jimmy Krsnak, 24009 465$^{th}$ Ave., Chester, SD (US) 57016

( * ) Notice: Subject to any disclaimer, the term of this patent is extended or adjusted under 35 U.S.C. 154(b) by 0 days.

(21) Appl. No.: 10/870,298

(22) Filed: Jun. 18, 2004

(65) Prior Publication Data

US 2005/0283870 P1 Dec. 22, 2005

(51) Int. Cl.
*A01H 5/00* (2006.01)

(52) U.S. Cl. ..... Plt./248
(58) Field of Classification Search ..... Plt./248
See application file for complete search history.

(56) References Cited

U.S. PATENT DOCUMENTS

PP2,614 P * 3/1966 Hauck ..... Plt./248 .....

OTHER PUBLICATIONS

Syringa, Appendix B, Plant Patents and Other Registrations [online], 2000. [Retrieved on Jan. 11, 2005]. Retrieved on the Internet: <http://www.tuinkrant.com/tkarchief/tk/info e/syringa e/app–b.htm>.*

* cited by examiner

* cited by examiner

*Primary Examiner*—Kent Bell
*Assistant Examiner*—June Hwu

(57) ABSTRACT

A new and distinct variety of lilac shrub developed from a sport of a *Syringa* sp. plant. This new plant is mainly distinguished by its striking display of non-standard variegated leaves.

3 Drawing Sheets

Latin name of the genus and species: Genus: *Syringa*. Species: sp.
Variety denomination: 'New Patriot Variegated-Lilac'.

CROSS REFERENCE TO RELATED APPLICATIONS

There are no related applications.

STATEMENT AS TO RIGHTS TO INVENTIONS MADE UNDER FEDERALLY-SPONSORED RESEARCH AND DEVELOPMENT

There are no Federal funds involved with this invention.

BACKGROUND OF THE INVENTION

1. Field of the Invention

The invention relates to a new and distinct variety of lilac shrub which is a member of the genus *Syringa* and the family Oleaceae. This new ornamental shrub herein after referred to as 'New Patriot Variegated-Lilac' was discovered in 1985 by Jimmy Krsnak in a lilac planting in Mitchell, S. Dak. The planting which had been made many years previous was part of an old farmstead. Sheep had been allowed to graze in the area where the lilacs were planted. The lilacs were in very poor condition and were unrecognizable as to their true habit and size. However, growing among them were stems, which appeared to have partially yellow leaves. The stems were dug up and their root severed from the rest of the roots of an old lilac belived to be *Syringa vulgaris*. The parent of 'New Patriot Variegated-Lilac' cannot now be verified. By the time the new plant was grown, propagated and found to maintain it's characteristics, the farmstead had been bulldozed out and the entire area developed into a new residential area. 'New Patriot Variegated-Lilac' is believed to be a sport of *Syringa vulgaris*.

2. Description of Relevant Prior Art

'New Patriot Variegated-Lilac' will become a valuable member of the lilac family because of the variegation of its leaves and its growth habit. Traditionally, lilacs are best known for their fragrant spring flowers. The variegation in 'New Patriot Variegated-Lilac' brings a second and even more striking aspect of color to the plant. Additionally, the smaller size and slower growth rate will allow the new plant to be used as a specimen plant. Original propagation of 'New Patriot Variegated-Lilac' was made by layering. Asexual propagation has since been made via stem grafts onto *Fraxinus pennsylvania* root stock under the supervision of Norm Evers, Director of McCrory Gardens on the South Dakota State University Campus. An additional two generations of 'New Patriot Variegated-Lilac' were asexually propagated by softwood cuttings by Jimmy Krsnak. In all cases the characteristics of the new plant remained stable. No attempts to sexually propagate 'New Patriot Variegated-Lilac' were made.

SUMMARY OF THE INVENTION

The following are the most outstanding characteristics of the 'New Patriot Variegated-Lilac', which distinguish it from all other lilac species and cultivars.

1. New leaves are variegated in a non-standard pattern that may or may not be aligned with the leaf veins.
2. The creamy-white variegation covers a range of ten percent to one hundred percent of individual leaves and includes both the upper and lower surfaces.

3. The variegation fades from the individual leaves as they age. After several months the creamy-white areas on some leaves may revert entirely to the dark blue-green color of older lilac leaves.
4. The variegation distinguishes 'New Patriot Variegated-Lilac' from all other lilacs including 'Dappled Dawn' which only shows variegation on the upper surface of the leaves.
5. Flowers are described a light violet-blue in color compared to bright purple-mauve for 'Dappled Dawn' Lilac.
6. 'New Patriot Variegated-Lilac' has a very slow to slow growth rate and reaches a height of eight to ten feet and a width of four to six feet.
7. The slower growth rate and smaller size also separate 'New Patriot Variegated-Lilac' from *Syringa vulgaris*.
8. The variegation, flowers, size and growth rate make this an excellent specimen plant.
9. 'New Patriot Variegated-Lilac' has survived temperatures of minus thirty degrees Fahrenheit.

BRIEF DESCRIPTION OF THE DRAWING

This new Lilac variety is illustrated by the accompanying photographic prints in which.

1.

2.

3.

Figure 1:
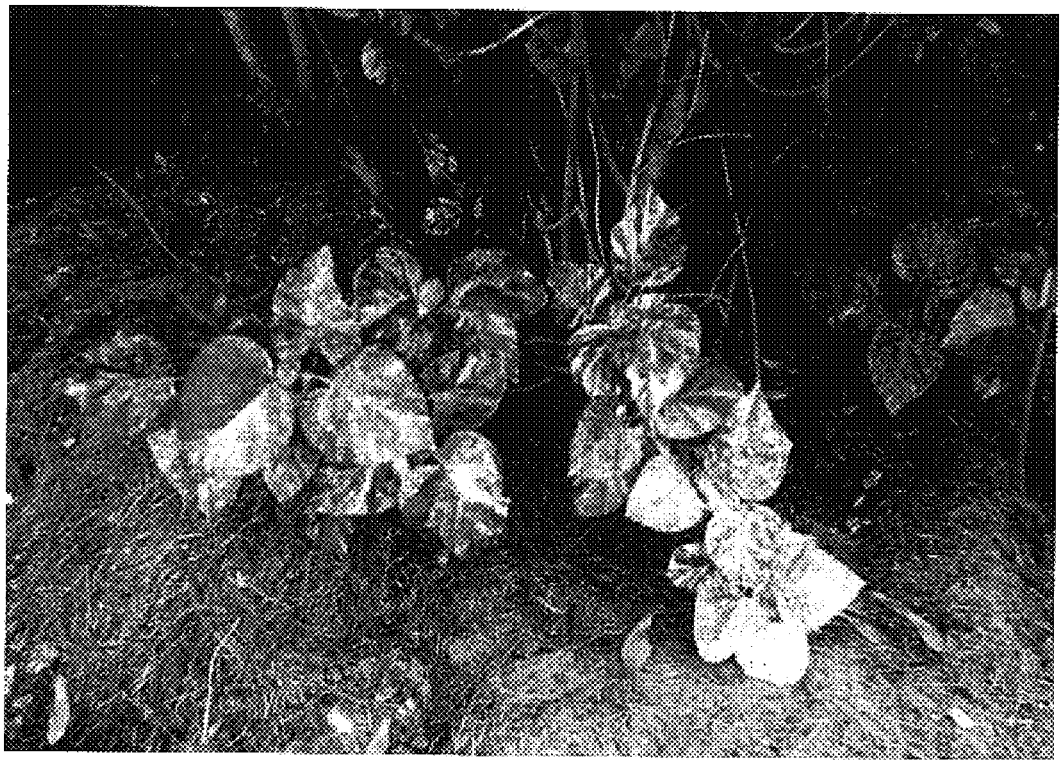
FIG. 1 is a close up of the leaves showing the typical, non-standard pattern of variegation of the new leaves.
Figure 2:
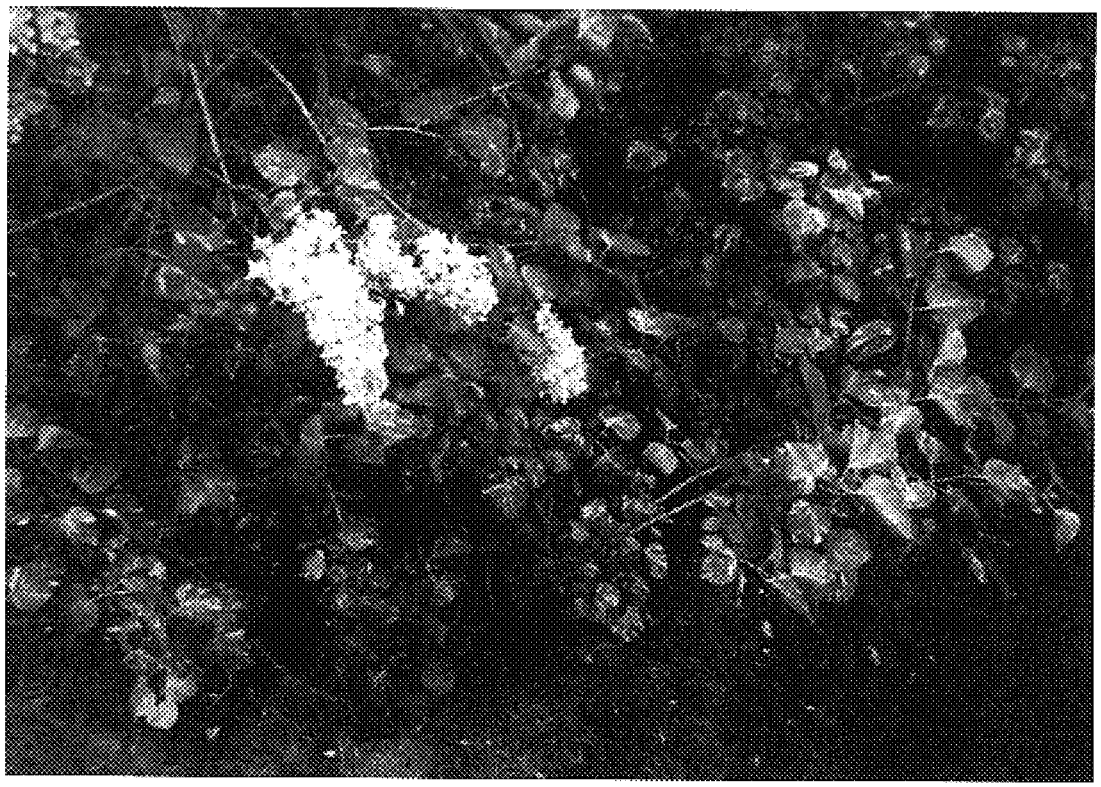
FIG. 2 shows the variegation throughout the plant and typical Lilac flowers.
Figure 3:
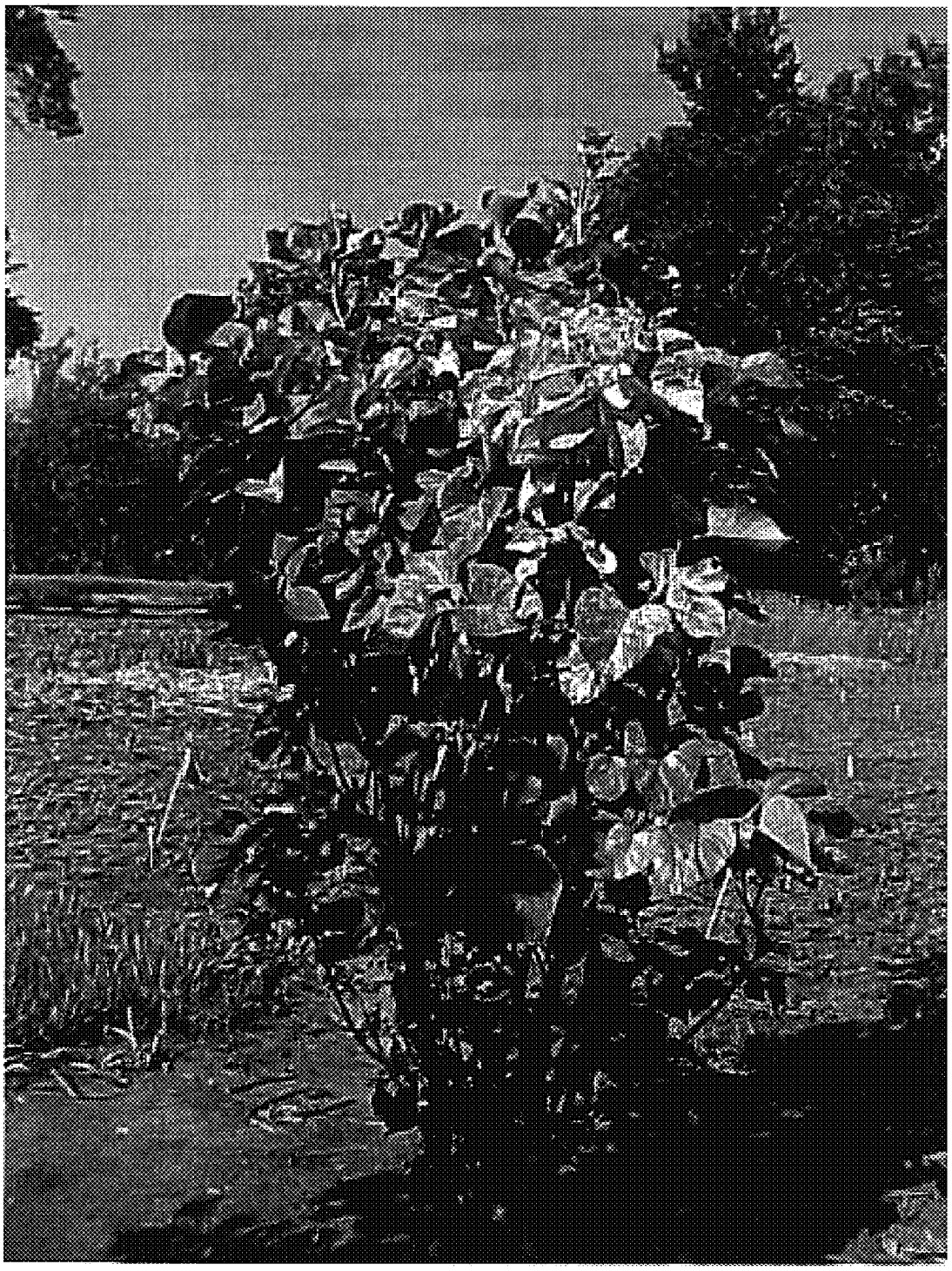
FIG. 3 shows the growth habit and the various stages of leaf growth.

The colors are as true as is reasonably possible to obtain by photographic illustration of this type.

BOTANICAL DESCRIPTION OF 'NEW PATRIOT VARIEGATED-LILAC'

The following is a detailed description of 'New Patriot Variegated-Lilac'. The chart used in identifying colors is the Pantone Library of Color Chart. Observations were made on plants that were growing in Eastern South Dakota, were varied in age from two years to ten years and were grown in variable conditions of full light to moderate shade.

1. Parentage: A sport of a *Syringa* plant believed to be *Syringa vulgaris*.
2. Botanical classification: *Syringa* sp. 'New Patriot Variegated-Lilac'.
3. Habit: Open leggy shrub with an upright, irregular outline.
4. Size: Eight to ten feet in height and four to six feet in width.
5. Growth rate: Very slow to slow.
6. Bark:
   - *a. Texture.*—Smooth.
   - *b. Color.*—Emerging new growth is light yellow-green P379C with streaks of light rose P210C. As the new branches mature, they become a darker yellow-green P384C changing to a green-brown P455C. Mature bark is 'Cool Gray' P6C.
   - *c. Lenticels.*—Abundant and measure up to one mm. Coloration is tan P4665C on matured bark. Lenticels on new growth are creamy-white in color, seventy percent to ninety percent lighter than pale yellow P100C.
7. Foliage:
   - *a. Leaf shape.*—Cordate.
   - *b. Arrangement.*—Opposite.
   - *c. Leaf apex.*—Acute to obtuse.
   - *d. Leaf base.*—Rounded to cordate.
   - *e. Leaf length.*—Approximate average is six cm.
   - *f. Leaf width.*—Approximate average is five cm.
   - *g. Leaf surface.*—Semi-glossy upper surface and non-glossy lower surface. The upper surface is relatively smooth while the under surface has protruding veins and a rougher texture resulting in a somewhat duller or matte appearance.
   - *h. Leaf margins.*—Entire.
   - *i. Leaf bud.*—Approximately two cm in length and diameter. Buds are reddish-brown color in the range of P497C, P498C and P499C.
   - *j. Color.*—Emerging leaves are variegated creamy-white to pale yellow and green with light rose P210C coloration on the edges and throughout the center of the leaf. The rose color is noticeable on both upper and lower surfaces of the leaves. The rose color fades completely from the leaf as it uncurls and starts maturing. The amount of variegation on the new leaves varies in individual leaves and can be anywhere from ten percent to one hundred percent of the leaf surface and is equally visible on upper and lower surfaces. While there are no patterns to the variegation, in some leaves the variegation may be aligned with the leaf veins. The color of the variegation of the new leaves can also vary but is generally a creamy-white in the range of seventy percent to ninety percent lighter than pale yellow P100C (both upper and lower surfaces). As individual leaves age, they gradually take on more varied yellow coloring, in the shades of P100C, P101C, P102C, P106C, and P107C (both upper and lower surfaces). As the leaf continues to mature it changes from yellow to green shades P369C and P370C (both upper and lower surfaces), and finally to a darker green P371C (upper surface only). The area of creamy-white color continues to diminish, but may not completely disappear from a fully mature leaf. Fully matured leaves are dark-green to a dark blue-green approximately fifty percent darker than P350C (upper surface only).
   - *k. Petioles.*—Average length is two cm. Average diameter is two mm. On new growth the petioles can vary in color, but are often a creamy-white in the range of seventy to ninety percent lighter than pale yellow P100C. The same light rose coloring P210C that appears on the leaves appears on the petioles. As the petioles grow, the colors change to yellow-green P393C, and then to a lighter green in the range of P365C and P366C. Petioles on mature leaves are a darker green P370C. The rose coloring on the petioles may linger for several weeks before gradually fading completely.
8. Flower morphology:
   - *a. Buds.*—As the buds begin to develop and show signs of color, they take on a red-blue color P258C. As the bud matures and is nearly ready to open, the color of the bud changes to a lighter red-blue color P256C.
   - *b. Flower.*—When the flower is fully open, the petals are a light violet-blue P2705. Individual flowers are tubular with four outer petals and four or eight inner petals. The four outer petals curve outward and back, while the four inner petals stand more upright. The very center of the flower is white. All of the flowers observed in the spring of 2005 were imperfect. None of them had either stamen or pistil.

*c. Flower size.*—Approximately one and one-half cm in length and width.

*d. Inflorescence.*—Flowers growing under shady conditions consisted of loosely packed panicles approximately sixteen cm in length and three to five cm in width. Panicles consist of approximately fourteen to eighteen racemes. Racemes consist of approximately ten to eighteen individual flowers. Flowers growing in full sunlight are the same approximate size but the racemes contained many more individual flowers.

*e. Fragrance.*—Soft, mild fragrance similar to but more subdued than *Syringa vulgaris.*

*f. Flowering time.*—Mid-May in USDA Hardiness Zone 4.

*g. Flower duration.*—Effective for seven to ten days.

9. Fruit: Capsules, of which very few are formed. A typical panicle may produce only eight to ten capsules.

10. Hardiness: Plants have been grown under observation at several locations in Eastern South Dakota including Brookings, S. Dak. Additional plants have been grown near Grand Forks, N. Dak. They have survived minus thirty degrees Fahrenheit with no apparent winter injury.

11. Culture: Prefers a well-drained soil. Conditions of full sunlight produce the best color contrast from the variegation and a much denser flower panicle.

12. Disease/pest resistance: The only problem observed has been powdery mildew on leaves which have reached approximately four months in age by mid-summer.

13. Landscape usage: Provides a very ornamental and hardy shrub which can be grown as a specimen plant, used in mass planting, or as an informal hedge.

It is claimed:

1. I claim a new and distinct variety of lilac shrub named 'New Patriot Variegated-Lilac' which is substantially as herein shown and described and which is distinguished by the variegation of it's leaves, flower color, growth rate and size.

* * * * *